(12) United States Patent
Klootwijk et al.

(10) Patent No.: US 10,302,590 B2
(45) Date of Patent: May 28, 2019

(54) INTEGRATED CIRCUIT WITH SENSING TRANSISTOR ARRAY, SENSING APPARATUS AND MEASURING METHOD

(71) Applicant: KONINKLIJKE PHILIPS N.V., Eindhoven (NL)

(72) Inventors: Johan Hendrik Klootwijk, Eindhoven (NL); Marleen Mescher, Eindhoven (NL); Pascal De Graaf, Eindhoven (NL); Bout Marcelis, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 40 days.

(21) Appl. No.: 14/434,559

(22) PCT Filed: Oct. 11, 2013

(86) PCT No.: PCT/IB2013/059296
§ 371 (c)(1),
(2) Date: Apr. 9, 2015

(87) PCT Pub. No.: WO2014/060916
PCT Pub. Date: Apr. 24, 2014

(65) Prior Publication Data
US 2015/0276667 A1 Oct. 1, 2015

Related U.S. Application Data

(60) Provisional application No. 61/714,400, filed on Oct. 16, 2012.

(51) Int. Cl.
*H01L 29/06* (2006.01)
*H01L 29/10* (2006.01)
(Continued)

(52) U.S. Cl.
CPC ..... *G01N 27/4148* (2013.01); *G01N 27/4146* (2013.01); *H01L 29/0673* (2013.01);
(Continued)

(58) Field of Classification Search
CPC ........... G01N 27/4148; G01N 27/4146; G01N 27/4141; G01N 27/4145; H01L 29/0673; H01L 29/1033; H01L 29/16
See application file for complete search history.

(56) References Cited

U.S. PATENT DOCUMENTS

2004/0136866 A1 7/2004 Pontis
2006/0188934 A1* 8/2006 Chang .................. B81B 3/0032
435/7.1
(Continued)

*Primary Examiner* — Robert J Eom

(57) ABSTRACT

An integrated circuit sensor array includes a semiconductor substrate; an insulating layer over the substrate; and a first transistor on the insulating layer. The first transistor includes an exposed functionalized channel region in between a source region and a drain region for sensing an analyte in a medium. The integrated circuit sensor array also includes a second transistor formed on the insulating layer, where the second transistor includes an exposed channel region between source and drain regions for sensing a potential of the medium. Further, a voltage bias generator is conductively coupled to the semiconductor substrate for providing the transistors with a bias voltage, the voltage bias generator being responsive to the second transistor.

18 Claims, 6 Drawing Sheets

(51) Int. Cl.
   *H01L 29/16*         (2006.01)
   *G01N 27/414*        (2006.01)
(52) U.S. Cl.
   CPC .......... *H01L 29/1033* (2013.01); *H01L 29/16*
                (2013.01); *G01N 27/4141* (2013.01); *G01N
                                              27/4145* (2013.01)

(56) References Cited

U.S. PATENT DOCUMENTS

| | | | |
|---|---|---|---|
| 2006/0246497 A1* | 11/2006 | Huang | G01N 27/4146 |
| | | | 435/6.14 |
| 2006/0263255 A1 | 11/2006 | Han | |
| 2008/0023325 A1 | 1/2008 | Mohapatra | |
| 2008/0121946 A1 | 5/2008 | Youn | |
| 2008/0210987 A1 | 9/2008 | Bondavalli | |
| 2010/0039126 A1* | 2/2010 | Chen | B82Y 15/00 |
| | | | 324/693 |
| 2010/0072976 A1 | 3/2010 | Sheu | |
| 2010/0219085 A1 | 9/2010 | Oviatt, Jr. | |
| 2010/0325073 A1 | 12/2010 | Haick | |
| 2011/0021894 A1* | 1/2011 | Mohanty | A61B 5/14532 |
| | | | 600/345 |
| 2011/0068015 A1 | 3/2011 | Park | |
| 2011/0147802 A1 | 6/2011 | Colli | |
| 2012/0036919 A1 | 2/2012 | Kamins | |

* cited by examiner

INTEGRATED CIRCUIT WITH SENSING TRANSISTOR ARRAY, SENSING APPARATUS AND MEASURING METHOD

This application is the U.S. National Phase application under 35 U.S.C. § 371 of International Application No. PCT/IB2013/059296, filed on Oct. 11, 2013, which claims the benefit of U.S. Provisional Application No. 61/714,400 filed on Oct. 16, 2012. These applications are hereby incorporated by reference herein.

FIELD OF THE INVENTION

The present invention relates to an integrated circuit (IC) comprising a semiconductor substrate, an insulating layer over said substrate and an array of transistors on said insulating layer including an first transistor comprising an exposed functionalized channel region in between a source region and a drain region for sensing an analyte in a medium.

The present invention further relates to a sensing apparatus including such an IC.

The present invention yet further relates to a method of measuring an analyte of interest in a medium using such an IC.

BACKGROUND OF THE INVENTION

The on-going miniaturization of semiconductor technology has enabled a remarkable diversification of functionality embedded in semiconductor devices such as integrated circuits (ICs), which in some cases has led to the provision of near-holistic solutions on a single device. For instance, semiconductor device miniaturization has led to the integration of one or more sensors into a single semiconductor device, and the deployment of such devices can be seen in widely different technical areas, e.g. automotive applications, healthcare applications, industrial gas flue monitoring and so on.

For instance, over the last few decades, sensing transistors have been added to ICs, e.g. chemical field effect transistors such as ion-sensitive field effect transistors (ISFETs), enzyme-functionalized field effect transistors sensitive to biomolecules (ENFETs) and so on. These field effect devices work on the principle that the channel region of the devices is exposed to the medium to be sensed, such that the current flowing through the channel region becomes a function of the analyte of interest. To this end, the device may comprise a functionalization layer separated from the channel region by a gate oxide or a functionalized extended gate acting as a floating gate, with the gate potential being defined by the level of interaction between the analyte of interest and the functionalization layer.

One of the major challenges in providing sensing functionality on an electronic device such as an IC is to ensure that the semiconductor device can be produced in an economically feasible manner. This is for instance a particular challenge when sensing elements of sub-micron dimensions, e.g. nano-elements such as nanowire-based transistors, are to be integrated in the semiconductor device, as it is not at all straightforward to manufacture such nano-elements using processing steps that are compatible with the manufacturing process of the overall semiconductor device. Hence, the integration of such dedicated elements can lead to a significant increase in the complexity of the manufacturing process of the semiconductor device, thereby significantly increasing the cost of such devices.

A particular problem in this respect is that when the sensing medium is a fluid, e.g. a liquid or gas, the sensor arrangement usually requires the presence of an external reference sensor or electrode to compensate for sensor drift, i.e. the time-varying response of a sensor to an analyte of interest. An example of such an arrangement is disclosed in US 2004/0136866 A1, in which a reference electrode is placed into contact with a fluid to be analysed in order to control the potential of the solution relative to the semiconductor nanowire sensing element. However, the inclusion of a reference sensor or electrode can further complicate the design of the sensor arrangement, which therefore can further increase the cost of the electronic device. Moreover, the surface of the reference electrode can be prone to fouling, in which case the sensor readings can become unreliable.

SUMMARY OF THE INVENTION

The present invention seeks to provide an IC according to the opening paragraph in which the need for a separate reference electrode is avoided.

The present invention further seeks to provide a sensing apparatus including such an IC.

The present invention yet further seeks to provide a method of measuring an analyte of interest using such an IC.

The invention as defined with the independent claims at least partly fulil the sought goals. The dependent claims provide advantageous embodiments.

In accordance with an aspect of the present invention, there is provided an integrated circuit as defined in the invention. The first transistor can be an analyte sensing transistor and the second transistor can be a medium sensing transistor.

The present invention has been based on the realization that the measurement of the analyte of interest using a field effect device can be performed at a time scale such that the total amount of charge in the medium is substantially constant during this time scale. In other words, the medium can be considered a closed or isolated system at the time scale of the measurement. This is of course applicable to truly closed systems, e.g. closed fluidic cells, but it is equally applicable to small local fluidic measurements that can be considered isolated from its environment at the time scales of the measurement. Consequently, due to the conservation of charge in the medium at this time scale, it can be demonstrated that the reference potential becomes a function of the back gate potential. Hence, by measuring the actual potential of the medium, i.e. the reference potential using an unfunctionalized field effect device, the back gate potential can be adjusted in response to the measured reference potential such that the desired reference potential is maintained in the medium, e.g. a fluid of interest without the need to provide a separate reference electrode for setting the potential of the medium.

The first transistor may be functionalized to sense the analyte of interest in any suitable manner. For instance, the functionalized channel region may be functionalized with a binding layer or instead may be functionalized by chemical modification of said channel region. Alternatively, the channel region may be exposed to the medium via an extended gate, i.e. a gate that is spatially separated from the channel region and is conductively coupled to the channel region by a metallization structure. An oxide layer such as an oxide film is typically present between the channel region and the functionalization layer to electrically insulate the channel region from the floating gate. The oxide film may have a functionalized outer surface to provide the functionalization layer.

In an embodiment, the IC comprises an array of transistors as defined in the invention. This has the advantage that a number of different analytes of interest, e.g. different gases or different biomolecules such as different DNA fragments, may be measured simultaneously. To this end, each of said first transistors may be individually functionalized, i.e. each first transistor may be functionalized to detect a different analyte of interest. The invention can then be used for fingerprinting. Alternatively multiple first transistors may be configured to sense the same analyte but with different sensitivity and/or detection level.

The present invention is particularly suitable for sensing ICs in which transistors having sub-micron dimension channel regions are provided, such as channel regions comprising a nanowire such as a silicon nanowire or a nanotube such as a carbon nanotube. For such ICs, the provision of a separate reference electrode is cumbersome and costly due to the fact that the reference electrode typically has to be provided separately and in a different form factor. Hence, the elimination of the need for a separate reference electrode by the present invention ensures that especially ICs containing such sub-micron dimensioned devices can be manufactured in a cost-effective manner. In particular, an IC comprising silicon nanowires can be manufactured using routinely available CMOS processing steps and can therefore be manufactured particularly cost effectively.

In accordance with another aspect of the present invention, there is provided a sensing apparatus as defined in the invention. Such a sensing apparatus benefits from a reliable an accurate determination of the presence and/or concentration of an analyte of interest in the sample in the sample compartment, e.g. a fluid flowing through a flow cell comprising the exposed first transistor, without the need for a separate reference electrode.

The sensing apparatus may further comprise a signal processor individually coupled to the respective sensing transistors, e.g. via bond pads on the IC that are conductively coupled to the source or drain regions of at least the one or more first transistors.

In accordance with another aspect of the present invention, there is provided a method of measuring an analyte of interest in a medium as defined in the invention.

The method of the present invention facilitates the accurate measurement of an analyte of interest in a fluid such as a gas or a liquid without the need for a reference electrode to control the potential of the fluid medium as already explained in more detail above.

In an embodiment, the method further comprises measuring the drain-source current flowing through the first transistor following said bias adjustment step; and deriving the presence of said analyte from said measured drain-source current. In particular, the measuring step may be performed at a time-scale such that the potential of said medium is constant during said measurement, as under these conditions the potential of the medium is a direct function of the back gate potential, such that this potential can be controlled by the back gate potential without the need for a separate reference electrode.

BRIEF DESCRIPTION OF THE EMBODIMENTS

Embodiments of the invention are described in more detail and by way of non-limiting examples with reference to the accompanying drawings, wherein:

FIG. 1 schematically depicts an aspect of an IC according to an embodiment of the present invention;

FIG. 2 schematically depicts another aspect of an IC according to an embodiment of the present invention;

Figure 5:
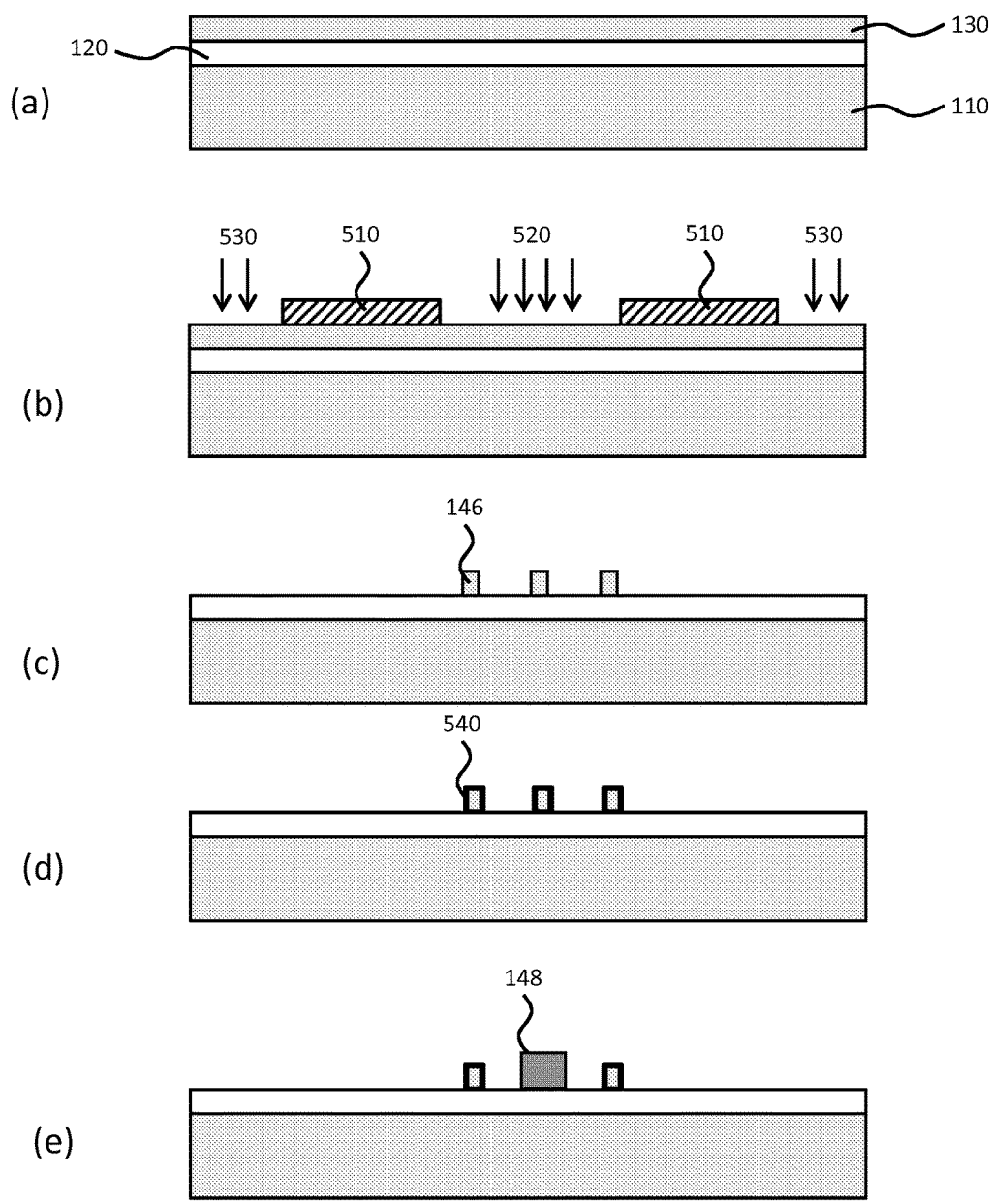
Figure 6:
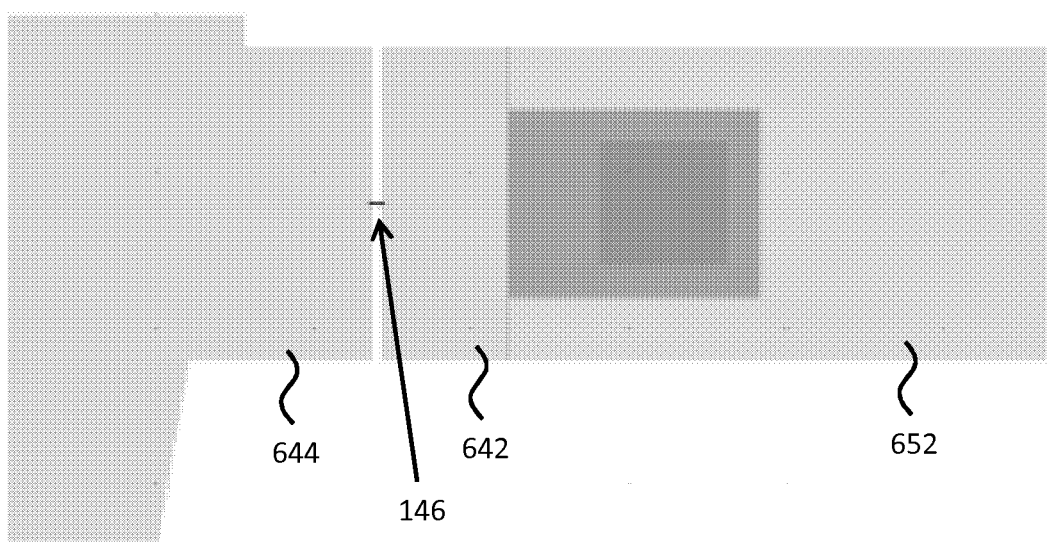

FIG. 5a-e schematically depict an embodiment of a method of manufacturing the IC of the present invention; and FIG. 6 schematically depicts a further aspect of an IC according to an embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

Figure 1:
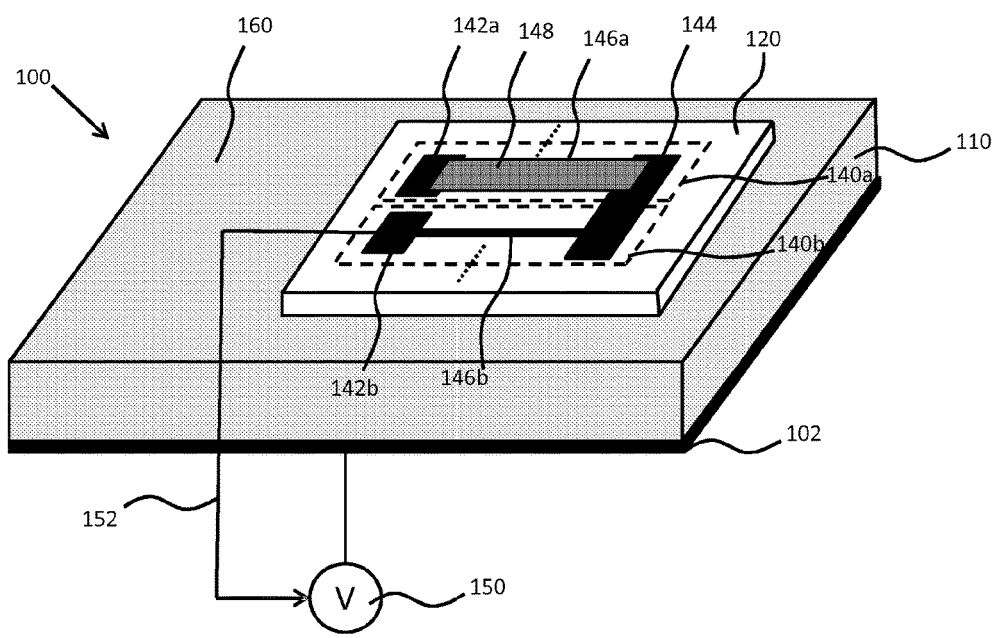

FIG. 1 schematically depicts an IC 100 comprising a silicon substrate 110, a patterned buried oxide layer 120 and a plurality of field effect transistors 140 that have a nanostructure such as a silicon nanowire or a carbon nanotube as channel region. The plurality of field effect transistors 140 may be arranged in an array. The plurality of field effect transistors 140 typically comprises at least one first transistor 140a with a silicon nanowire channel region 146a extending between a source region 142a and a common drain region 144, although it should be understood that the field effect transistors of the IC 100 may have any suitable channel region structure. In particular, other sub-micron dimension channel region structures such as nanowires of different materials, or different nanostructures such as single-walled or multi-walled nanotubes, e.g. carbon nanotubes are equally feasible.

In the context of the present invention, a nanowire is a conductive or semiconductive structure having a cross-section of sub-micron dimensions and having a length that may range from several hundreds of nanometers to several micron. The nanowire may be a solid or hollow structure, and may have a circular or non-circular, e.g. square or rectangular cross-section. The term 'nanotube' in the present application is intended to include single or multi-walled nanotubes. In a preferred embodiment, the nanowire is a silicon nanowire, which preferably has an oxidized outer surface, as will be explained in more detail later.

The exposed surface of the channel region 146a of an first transistor 140a is typically functionalized with a functional or binding layer 148, which may be deposited on top of the channel region 146a using any suitable deposition technique, e.g. spin-coating, or may be formed by chemically modifying the channel region 146a, or the exposed surface of a gate oxide over the channel region 146a, for instance by forming hydrogen groups or (3-Aminopropyl)triethoxysilane (APTES) groups by silanization of the exposed surface of the gate oxide. The functionalization of such sensing surfaces is well known per se to the skilled person e.g. from the technical field of ChemFETs, and the nature of the functionalization of the channel region 146a is not essential to the present invention, such that the present application will not disclose this in any further detail for the sake of brevity only.

The IC 100 further comprises a preferably unfunctionalized field effect transistor 140b, which is intended to measure the potential of the medium or fluid to which the sensing field effect transistors 140a, 140b of the IC 100 are exposed during the operation of the IC 100. The second transistor 140b has a channel region 146b, e.g. a silicon nanowire channel region or any other suitable channel region structure as previously explained that extends between a source region 142b and a common drain region 144. The first channel region 146a and the second channel region 146b thus share a drain region for providing the nanowire channel regions with a common drive current, with the individual source regions 142a and 142b allowing measurement of the current induced through individual nanowire channel regions 146a and 146b. It should be understood that this arrangement is by way of non-limiting example only; it is equally feasible for the sensing transistors 140 to share a source region and have individual drain regions, or to have individual source and drain regions, although the latter complicates the manufacturability of the IC 100 due to the fact that a larger number of contacts to these individual regions has to be provided.

The IC 100 further comprises a bias voltage generator 150 that is conductively coupled to the semiconductor substrate 110, e.g. via a back gate contact 102, which may be realized using any suitable conductive material, e.g. a metal such as Au, Al, Ti and/or Cu. The bias voltage generator 150 causes the substrate 110 to act as a common gate for the sensing transistors 140a, 140b of the IC 100, with the oxide layer 120 between the substrate 110 and the channel regions 146a, 146b acting as a bottom gate oxide. The bias voltage generator 150 is conductively coupled to the second transistor 140b and is responsive to the potential sensed by the second transistor 140b. Specifically, the bias voltage generator 150 is arranged to keep the potential of the medium at a predefined value by adjusting the bias voltage that is applied to the substrate 110.

Figure 2:
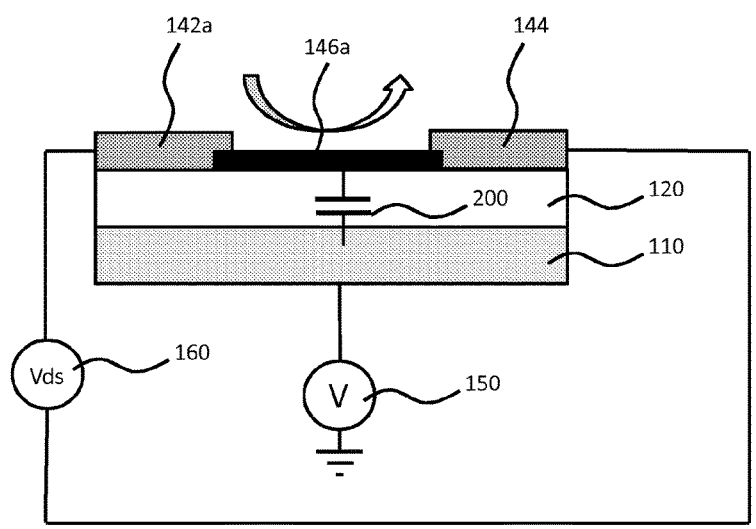

This can be better understood by reference to FIG. 2, which schematically shows a cross-section of the IC 100 according to an embodiment of the present invention. As can be seen in FIG. 2, the substrate 110 is capacitively coupled to the nanowire channel region 146a of the first transistor 140a as symbolically demonstrated by capacitor 200 (in fact the substrate 110 is capacitively coupled to all sensing transistors 140a, 140b on the bottom gate oxide 120). In addition, the nanowire channel region 146a is capacitively coupled to the medium indicated by the curved arrow via the upper gate oxide (not shown), such that the arrangement in FIG. 2 equates to a stacked capacitor arrangement.

Consequently, by manipulation of the bias voltage provided by the bias voltage generator 150, the potential of the medium can be adjusted as long as the amount of charge in the medium remains constant during the sensing period of the IC 100 due to the fact that the variable bias potential of the substrate 110 is capacitively coupled to the medium. This is always the case for truly closed systems but is equally the case for open systems where a small volume of the overall system volume can be considered isolated from the rest of the volume at the time scale of the measurement. Hence, the current flowing through the nanowire channel region 146a extending between the drain region 144 and the source region 142 as governed by the drain-source potential difference induced by current source 160 can be directly related to the presence, e.g. the concentration, of the analyte of interest in the medium as the potential of the medium is well-defined.

In an embodiment, the bias voltage generator 150 may implement a feedback loop in which the bias voltage is adjusted in response to the medium potential measured by the second transistor 140b, e.g.:

REPEAT
IF ($V_{medium} > V_{set}$) THEN $V_{bias} := V_{bias} - x$
IF ($V_{medium} < V_{set}$) THEN $V_{bias} := V_{bias} + x$
UNTIL $V_{medium} = V_{set}$ in which $V_{medium}$ is the medium of the potential, $V_{set}$ is the target potential of the medium, $V_{bias}$ is the bias voltage applied by the bias voltage generator 150 to the substrate 110 and x is a positive number that defines the amount by which $V_{bias}$ is adjusted. The amount x may be a fixed, i.e. predefined amount, or may be an amount that is dynamically determined based on the difference between $V_{medium}$ and $V_{set}$. As will be apparent from the above algorithm, the bias voltage generated by the bias voltage generator 150 is incrementally adjusted, i.e. reduced when $V_{medium}$ exceeds $V_{set}$ or increased when $V_{set}$ exceeds $V_{medium}$ until $V_{set}$ equals $V_{medium}$. Any suitable adjustment step frequency may be employed, as long as the step frequency is high enough to ensure that the analyte measurement may be completed rapidly enough to ensure that the assumption that the medium contains a constant charge still holds, which is particularly relevant to open fluid systems for which a measurement volume is considered as a closed sub-system at the time scale of the measurement as previously explained. Typically, the above assumption is valid for any measurement performed in the millisecond range or shorter.

It should be understood that the above feedback algorithm is given by way of non-limiting example only and that any suitable feedback mechanism may be used to adjust the bias voltage applied to the substrate 110. Also, although the bias voltage generator 150 may include control circuitry for implementing the aforementioned feedback mechanism, it should be understood that it is equally feasible that the IC 100 comprises a separate control circuit for receiving the medium potential reading from the second transistor 146b and providing the bias voltage generator 150 with an appropriate control signal. For instance, such a control circuit may form part of a signal processor of the IC 100, which for instance may be further adapted to process the first signals from the one or more first transistors 146a. Other suitable arrangements will be immediately apparent to the skilled person.

At this point, it is noted that the IC 100 may comprise a plurality of first transistors 146a, which for instance may be organized in an array further comprising one or more of the second transistors 146b. In an embodiment, at least some of the first transistors 146a comprise different functionalization layers 148, such that different analytes of interest can be detected in a single measurement of the IC 100.

It is further noted that the drive current applied to the shared drain 144 of the array of FETs 140 may have any suitable form, e.g. a direct current or an alternating current. In case of the application of an alternating current, the impedance of the nanowires will have a complex form, i.e. comprise a real and an imaginary part. This further enhances the selectivity of a sensing FET 140, and further facilitates the detectability of materials or particles of a particular size due to the fact that the impedance will exhibit a large variation when the alternating current matches the resonance or Eigen frequency of the translational or rotational modes of the particles.

The IC 100 may further comprise a signal processor (not shown) for processing the signals produced by the FETs 140. Such a signal processor may be coupled to the individual source regions 142a, 142b for this purpose by way of non-limiting example only, as it will be readily understood by the skilled person that any suitable conductive coupling between the analyte and transistors 140a, 140b and the signal processor may be applied.

The signal processor may be adapted to derive an analyte measurement from the first transistor signal acquired during said signal acquisition period, i.e. the period in which the one or more first transistors 140a and second transistors 140b are enabled by the bias voltage generator 150. As the interpretation of the acquired signals is well-known per se, this will not be explained in any further detail for the sake of brevity only.

In an alternative embodiment, the signal processor may be omitted from the IC 100, in which case e.g. the source regions 142a, 142b may be conductively coupled to externally accessible bond pads to facilitate off-chip evaluation of the sensing signals of the sensing transistors 140a, 140b.

Figure 3A:
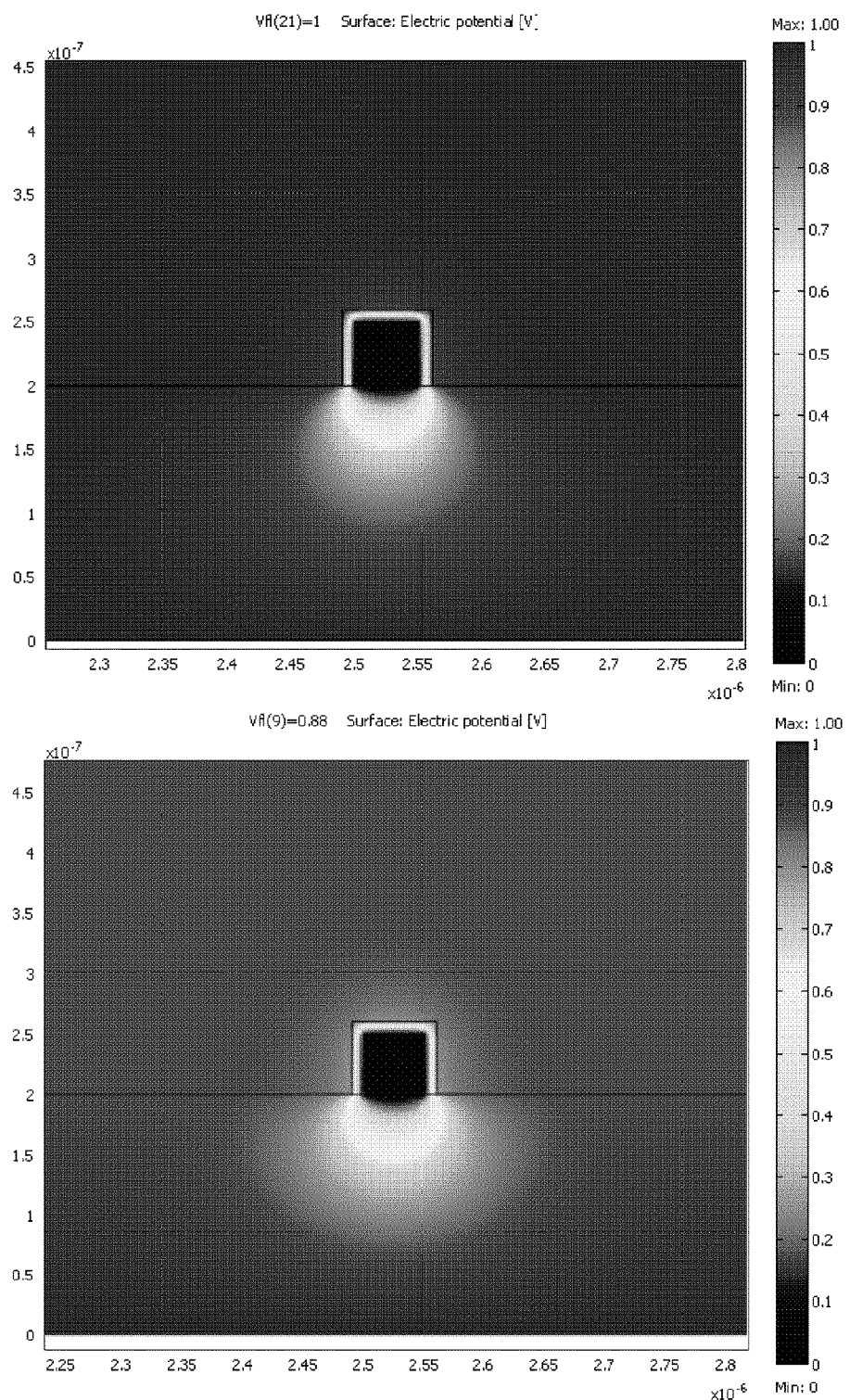
FIG. 3a depicts a contour plot of the potential generated in a solution by a reference electrode (top pane) and by the back gate bias control principle of the present invention (bottom pane)
Figure 3B:
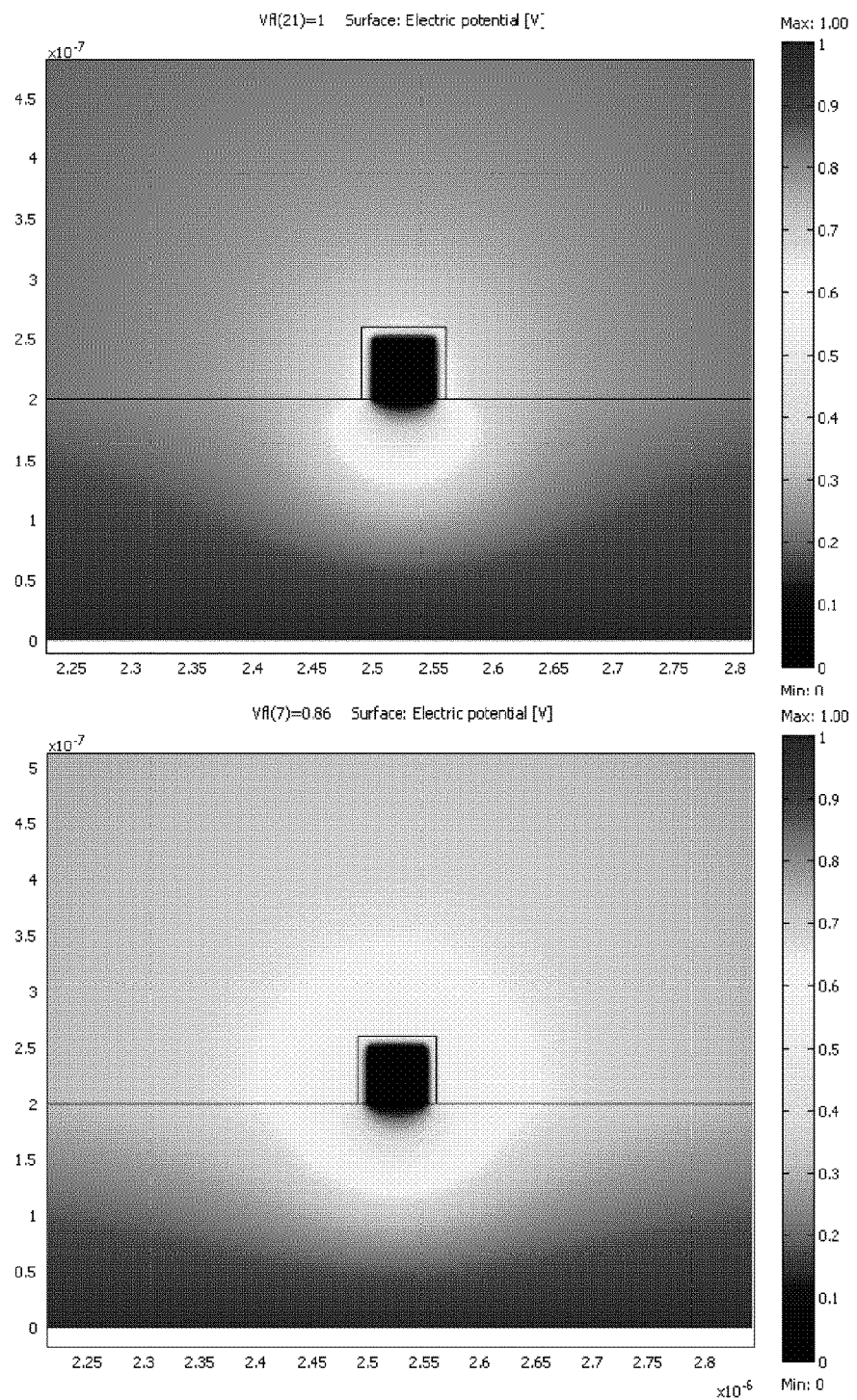
FIG. 3b depicts a contour plot of the potential generated in another solution by a reference electrode (top pane) and by the back gate bias control principle of the present invention (bottom pane)

FIG. 3a and FIG. 3b show the surface electric potentials of a $10^{-1}$M NaCl solution (FIG. 3a) and a $10^{-6}$M NaCl solution (FIG. 3b) generated by a reference electrode (top panes) and by the back gate biasing approach of the present invention (bottom panes). This clearly demonstrates that it is entirely feasible to obtain the desired potential in the medium of interest (here different aqueous NaCl solutions) with the back gate biasing technique of the present invention.

Figure 4:
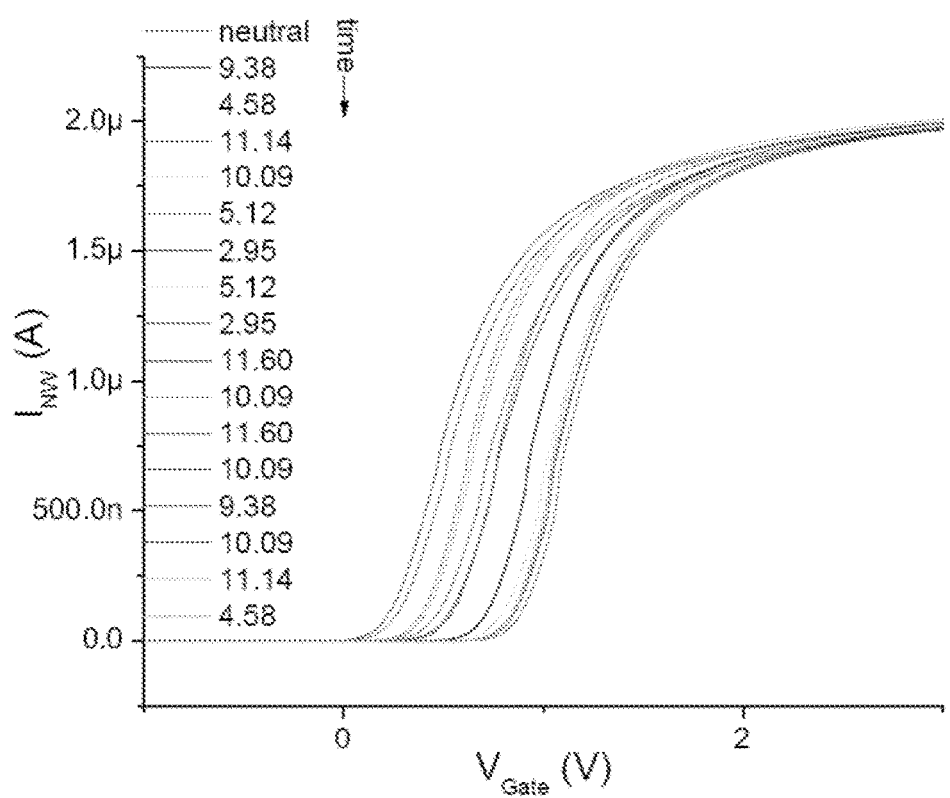
FIG. 4 depicts an experimentally obtained response from a Si-nanowire FET exposed to various NaCl solutions when biased using a back gate bias voltage waveform according to an embodiment of the present invention.

FIG. 4 depicts the measurement results obtained by exposing a Si-nanowire FET 140a formed in a silicon-on-insulator (SOI) substrate and functionalized as a pH sensor by covering the silicon nanowire 146 with for instance an $Al_2O_3$ film, a $SiO_2$ film optionally functionalized with APTES, and so on. The sensor was exposed to a number of aqueous samples of different pH each comprising dissolved $Na^+$ and $Cl^-$ ions. For each pH measurement, the bias voltage generator 150 was responsive to the second transistor 140b to ensure that the potential of the NaCl solution was kept at the desired potential. In each case, the pH could be accurately obtained from the sensor response, thus clearly demonstrating that by adjusting the bias voltage applied to the substrate 110 in response to the sensed potential of the medium, i.e. the various NaCl solutions, the pH of each solution could be accurately determined.

An example method of manufacturing an IC 100 is schematically depicted in FIG. 5. In step (a), a substrate 110 is provided that carries an electrically insulating layer 120 and a semiconductor material layer 130. Preferably, this arrangement is provided as a silicon on insulator substrate in which layers 110 and 130 are silicon layers separated by a buried oxide layer 120, but it should be understood that the layer stack as shown in step (a) may be provided in any suitable manner using any suitable materials. A conductive contact 102 (not shown), e.g. a metal contact, may also be present or formed at any suitable point in the method to provide the substrate 110 with a back gate contact such that the substrate 110 can be used as a back gate.

In a next step (b), a patterned mask 510 is formed on the silicon layer 130 that defines the regions into which impurities are to be implanted, after which such impurities are implanted into the silicon layer 130, such as impurities 520, e.g. $N^-$-type impurities, in the region in which the nanowire channel regions 146 are to be formed and impurities 530, e.g. N++-type impurities, in the source and drain regions 142 and 144. As the formation of such a mask and such implantation steps are routine practice for the skilled person, they will not be explained in any further detail for the sake of brevity only.

Subsequently, the mask 510 is removed from the silicon layer 130, which is subsequently patterned to form the nanowires 146 and the source and drain regions 142 and 144, as shown in step (c). It is noted that the cross-section of the IC 100 shown in step (c) is rotated 90° compared to the cross-sections shown in step (a) and (b), such that the formed source and drain regions 142 and 144 are not shown in the cross-section of step (c). The patterning of the silicon layer 130 may be achieved in any suitable manner. Particularly preferred is the use of electron beam lithography to form the nanowires 146, which may be combined with a dry etch to form the source regions 142 and the drain region(s) 144.

Step (d) is an optional step, which is however preferred to ensure that the medium to which the nanowires 146 are exposed acts as a floating gate on the channel regions of the field effect transistors 140 including the nanowire channel regions 146. In step (d), the nanowires 146 are provided with an oxide layer 540. In case of silicon nanowires 146, this is preferably achieved by the partial oxidation of the silicon, e.g. by exposing the silicon nanowires 146 to an oxide-rich environment at elevated temperatures, e.g. 300° C. or higher for a period of time. This oxide layer 540 thus acts as an upper gate oxide when the nanowires 146 are brought into contact with the medium.

Next, selected nanowires 146 may be functionalized with a functionalization or binding layer 148 as shown in step (e). The one or more binding layer portions 148 may be formed in any suitable way, e.g. by deposition of a binding layer over all nanowires 146 and the selective removal of the binding layer material from those nanowires 146 that are not to be used as sensing nanowires for the analyte having affinity with the binding layer 148, or alternatively by the selective deposition of the binding layer 148 over only those nanowires 146 that are to be sensitive to the analyte of interest having affinity with the binding layer 148. Different nanowires 146 may be functionalized with different binding layers 750 as will be apparent to the skilled person. As many of such binding layer materials are well-known per se, it suffices to say that any suitable binding material may be used.

Due to the fact that the spacing between nanowires 140 is many factors larger than the cross-section or thickness of a single nanowire 140, such a selective deposition can be achieved using techniques that are routinely available to the skilled person. FIG. 6 schematically depicts a top view of a single FET 140 including source contact 642, drain contact 644, the metal 652 in conductive contact with the source contact 642 (the metal contacting the drain contact has been omitted for the sake of clarity) and the nanowire 146. This clearly demonstrates that there is ample room for the selective deposition of the binding layer 148 over the nanowire 146.

The IC 100 may be integrated in any suitable sensing apparatus. Such a sensing apparatus typically comprises a sample compartment for receiving a stationary sample of or a flowing sample, in which case the sample compartment may comprise a flow channel, which may have any suitable dimensions. The IC 100 is typically placed such that the sensing transistors 140a and 140b are exposed in the sample compartment. Such a sensing apparatus may for instance be a microfluidics-based sensing apparatus or an assay-based sensing apparatus to be used in a healthcare application, an exhaust gas sensing apparatus to be used in a domestic, industrial or automotive application and so on. Analytes of interest may include gases such as $O_2$, CO, $CO_2$, $NO_x$ and so on, micro-organisms such as viruses and bacteria, heavy metals, pesticides, drugs, glucose, haematocrit, and other relevant body substances that can be detected in a bodily fluid such as saliva, urine or blood. Many other suitable application domains and analytes of interest for such a sensing apparatus will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
   a semiconductor substrate;
   an insulating layer over said semiconductor substrate;
   a first transistor on said insulating layer; and
   a second transistor on said insulating layer,
   wherein the first transistor includes a first source region, a first drain region, and a functionalized channel region in between the first source region and the first drain region, wherein the functionalized channel region is senses at least one of a presence or a concentration of an analyte of interest in a medium in response to the functionalized channel region being exposed to the medium, via a flow channel sample compartment, during a signal acquisition period of the integrated circuit,
   wherein the second transistor includes a second source region, a second drain region, and an unfunctionalized channel region in between the second source region and the second drain region, wherein the unfunctionalized channel region is (i) unfunctionalized to not bind analytes and (ii) senses a potential of the medium $V_{medium}$ in response to the unfunctionalized channel region being exposed to the medium, via the flow channel sample compartment, during the signal acquisition period of the integrated circuit, and wherein (a) the first and second source regions comprise a common source region or (b) the first and second drain regions comprise a common drain region, to provide the functionalized and unfunctionalized channel regions with a common drive current;
   a voltage bias generator conductively coupled to the semiconductor substrate for applying, in response to a control signal, a back gate potential bias voltage $V_{bias}$ to the semiconductor substrate during the signal acquisition period of the integrated circuit; and
   a signal processor individually coupled to the first and second transistors, and coupled to the voltage bias generator, wherein the signal processor provides the control signal to the voltage bias generator during the signal acquisition period of the integrated circuit, wherein the signal processor determines, via the second transistor, a potential of the medium $V_{medium}$ in response to an application of the back gate potential bias voltage $V_{bias}$ to the semiconductor substrate during the signal acquisition period of the integrated circuit, further wherein the voltage bias generator is responsive to the control signal to incrementally adjust the back gate potential bias voltage $V_{bias}$ at an adjustment step frequency that ensures a completion of an analyte measurement, via the first transistor and the signal processor, during the signal acquisition period of the integrated circuit for as long as an amount of charge in the medium remains constant during the signal acquisition period, and wherein the incremental adjustment of the back gate potential bias voltage $V_{bias}$ includes repeating the steps of (i) reducing $V_{bias}$ in response to the determined $V_{medium}$ exceeding a target potential, $V_{set}$, of the medium until $V_{medium}$ equals $V_{set}$, and (ii) increasing $V_{bias}$ in response to the determined $V_{medium}$ being less than the target potential $V_{set}$ of the medium until $V_{medium}$ equals $V_{set}$.

2. The integrated circuit of claim 1, wherein said functionalized channel region is functionalized with a binding layer for binding the analyte of interest.

3. The integrated circuit of claim 1, wherein said functionalized channel region is functionalized by chemical modification of said channel region.

4. The integrated circuit of claim 1, further comprising an array of transistors, said array comprising a plurality of said first transistors and a plurality of said second transistors.

5. The integrated circuit of claim 4, wherein each of said first transistors is individually functionalized.

6. The integrated circuit of claim 1, wherein each channel region comprises a nanowire or a nanotube.

7. The integrated circuit of claim 6, wherein the nanowire comprises of a silicon nanowire.

8. The integrated circuit of claim 6, wherein the nanotube comprises of a carbon nanotube.

9. The integrated circuit of claim 1, wherein each channel region is covered by an oxide film.

10. The integrated circuit of claim 1, wherein the voltage bias generator is conductively coupled to the semiconductor substrate via a back gate contact for causing the substrate to act as a common gate for the first and second transistors, the insulating layer being a bottom gate oxide, and the exposed unfunctionalized channel region being capacitively coupled to the medium via an upper gate oxide located over the exposed unfunctionalized channel region.

11. The integrated circuit of claim 1, wherein the signal processor further determines an analyte measurement in response to the first signal provided by the first transistor.

12. A sensing apparatus comprising:
   a sample compartment; and
   an integrated circuit, wherein the integrated circuit comprises:
   a semiconductor substrate;
   an insulating layer over said semiconductor substrate;
   a first transistor on said insulating layer; and
   a second transistor on said insulating layer,
   wherein the first transistor includes a first source region, a first drain region, and a functionalized channel region in between the first source region and the first drain region, wherein the functionalized channel region senses at least one of a presence or a concentration of an analyte of interest in a medium in response to the functionalized channel region being exposed to the medium, via the sample compartment, during a signal acquisition period of the integrated circuit, wherein the second transistor includes a second source region, a second drain region and an unfunctionalized channel region in between the second source region and the second drain region, wherein the unfunctionalized channel region is (i) unfunctionalized to not bind analytes and (ii) senses a potential of the medium in response to the unfunctionalized channel region being exposed to the medium, via the sample compartment, during the signal acquisition period of the integrated circuit, and wherein (a) the first and second source regions comprise a common source region or (b) the first and second drain regions comprise a common drain region, to provide the functionalized and unfunctionalized channel regions with a common drive current, the integrated circuit further comprising:

a voltage bias generator conductively coupled to the semiconductor substrate, wherein the voltage bias generator applies, in response to a control signal, a back gate potential bias voltage $V_{bias}$ to the semiconductor substrate during the signal acquisition period of the integrated circuit; and a signal processor individually coupled to the first and second transistors, and coupled to the voltage bias generator, wherein the signal processor provides during the signal acquisition period of the integrated circuit the control signal to the voltage bias generator, wherein the signal processor determines, via the second transistor, a potential of the medium $V_{medium}$ in response to an application of the back gate potential bias voltage $V_{bias}$ to the semiconductor substrate during the signal acquisition period of the integrated circuit, further wherein the voltage bias generator incrementally adjusts, in response to the control signal, the back gate potential bias voltage $V_{bias}$ at an adjustment step frequency that ensures a completion of an analyte measurement, via the first transistor and the signal processor, during the signal acquisition period of the integrated circuit for as long as an amount of charge in the medium remains constant during the signal acquisition period, and wherein the incremental adjustment of the back gate potential bias voltage $V_{bias}$ includes repeating the steps of (i) reducing $V_{bias}$ in response to the determined $V_{medium}$ exceeding a target potential, $V_{set}$, of the medium until $V_{medium}$ equals $V_{set}$, and (ii) increasing $V_{bias}$ in response to the determined $V_{medium}$ being less than the target potential $V_{set}$ of the medium until $V_{medium}$ equals $V_{set}$.

13. The sensing apparatus of claim 12, wherein said sample compartment comprises a flow channel.

14. The sensing apparatus of claim 12, wherein the signal processor further determines an analyte measurement in response to the first signal provided by the first transistor.

15. A method of measuring an analyte of interest in a medium, the method comprising acts of:

exposing, via a flow channel sample compartment, the medium including said analyte of interest to a first transistor and a second transistor of an integrated circuit, wherein the integrated circuit comprises a semiconductor substrate, an insulating layer over the semiconductor substrate, and the first and second transistors on the insulating layer, wherein the first transistor includes a first source region, a first drain region, and a functionalized channel region in between the first source region and the first drain region, wherein the functionalized channel region is operable for sensing at least one of a presence or a concentration of the analyte of interest in the medium in response to the functionalized channel region being exposed to the medium, via the flow channel sample compartment, during a signal acquisition period of the integrated circuit, wherein the second transistor includes a second source region, a second drain region, and an unfunctionalized channel region in between the second source region and the second drain region, wherein the unfunctionalized channel region is (i) unfunctionalized to not bind analytes and (ii) operable for sensing a potential of the medium $V_{medium}$ in response to the unfunctionalized channel region being exposed to the medium, via the flow channel sample compartment, during the signal acquisition period of the integrated circuit, and wherein (a) the first and second source regions comprise a common source region or (b) the first and second drain regions comprise a common drain region, to provide the functionalized and unfunctionalized channel regions with a common drive current;

applying, via a voltage bias generator conductively coupled to the semiconductor substrate and in response to a control signal of a signal processor coupled to the voltage bias generator, a back gate potential bias voltage $V_{bias}$ to the semiconductor substrate during the signal acquisition period of the integrated circuit;

sensing, via the second transistor and the signal processor coupled to the second transistor, a potential of the medium $V_{medium}$ in response to the application of the back gate potential bias voltage $V_{bias}$ to the semiconductor substrate during the signal acquisition period of the integrated circuit; and incrementally adjusting, via the voltage bias generator and the control signal of the signal processor coupled to the voltage bias generator, the back gate potential bias voltage $V_{bias}$ at an adjustment step frequency that ensures a completion of an analyte measurement, via the first transistor and the signal processor coupled to the first transistor, during the signal acquisition period of the integrated circuit for as long as an amount of charge in the medium remains constant during the signal acquisition period, and wherein the incremental adjustment of the back gate potential bias voltage $V_{bias}$ includes repeating the steps of (i) reducing $V_{bias}$ in response to the sensed $V_{medium}$ exceeding a target potential, $V_{set}$, of the medium until $V_{medium}$ equals $V_{set}$, and (ii) increasing $V_{bias}$ in response to the sensed $V_{medium}$ being less than the target potential $V_{set}$ of the medium until $V_{medium}$ equals $V_{set}$.

16. The method of claim 15, further comprising acts of:

measuring, via the signal processor, a drain-source current flowing through the first transistor following said bias adjustment act; and deriving, via the signal processor, a presence of said analyte from said measured drain-source current.

17. The method of claim 16, wherein said measuring act is performed during a period of time a potential of said medium is constant.

18. The method of claim 15, further comprising the step of determining, via the signal processor, an analyte measurement in response to a first signal provided by the first transistor.

* * * * *